United States Patent
Grodzins (10) Patent No.: US 7,391,508 B2
(45) Date of Patent: Jun. 24, 2008

(54) ARC/SPARK OPTICAL EMISSION SPECTROSCOPY CORRELATED WITH SPARK LOCATION

(75) Inventor: Lee Grodzins, Lexington, MA (US)

(73) Assignee: Thermo NITON Analyzers LLC, Billerica, MA (US)

( * ) Notice: Subject to any disclaimer, the term of this patent is extended or adjusted under 35 U.S.C. 154(b) by 141 days.

(21) Appl. No.: 11/486,439

(22) Filed: Jul. 13, 2006

(65) Prior Publication Data

US 2007/0019182 A1    Jan. 25, 2007

Related U.S. Application Data

(60) Provisional application No. 60/700,664, filed on Jul. 20, 2005.

(51) Int. Cl.
*G01J 3/443* (2006.01)
*G01N 21/17* (2006.01)
*G01N 21/63* (2006.01)
*G01N 21/67* (2006.01)

(52) U.S. Cl. .................. 356/72; 356/313; 356/318

(58) Field of Classification Search .......... 356/72, 356/313, 318
See application file for complete search history.

(56) References Cited

U.S. PATENT DOCUMENTS

| | | | |
|---|---|---|---|
| 4,641,250 A | 2/1987 | Strong | 364/507 |
| 4,804,603 A | 2/1989 | Liston | 430/45 |
| 4,956,824 A | 9/1990 | Sindeband et al. | 367/129 |
| 4,973,800 A | 11/1990 | Sindeband et al. | 178/18 |
| 5,009,277 A | 4/1991 | Sindeband et al. | 178/18 |
| 5,050,134 A | 9/1991 | Butler | 367/118 |
| 5,216,482 A * | 6/1993 | Fukui et al. | 356/313 |
| 5,216,817 A | 6/1993 | Misevich et al. | 33/515 |
| 5,252,834 A * | 10/1993 | Lin | 356/318 |
| 5,308,936 A | 5/1994 | Biggs et al. | 178/18 |
| 5,379,269 A | 1/1995 | Sindeband et al. | 367/127 |
| 6,008,896 A | 12/1999 | Sabsabi et al. | 356/318 |
| 6,359,687 B1 | 3/2002 | Cheng | 356/318 |
| 6,466,309 B1 | 10/2002 | Kossakovski et al. | 356/73 |
| 2002/0130668 A1 | 9/2002 | Blades | 324/536 |
| 2003/0197125 A1 | 10/2003 | De Saro et al. | 250/339.07 |
| 2004/0199079 A1 | 10/2004 | Chuck et al. | 600/477 |

FOREIGN PATENT DOCUMENTS

EP    0 396 291 A2    11/1990

OTHER PUBLICATIONS

International Search Report; dated Feb. 5, 2007; received Feb. 9, 2007; PCT/US2006/027374.

(Continued)

*Primary Examiner*—F. L Evans
(74) *Attorney, Agent, or Firm*—Bromberg & Sunstein LLP (57) ABSTRACT

Two or more high-frequency microphones are used to determine where an individual spark or other excitation beam strikes a sample in an optical emission spectroscopy (OES) instrument. The position of the spark can be correlated with the elemental composition of the material in the sample vaporized by the spark. The microphones are placed appropriately in air around a sparker of the instrument, or appropriately on the sample, or on both the sample and in the air. Arrival times of sound from the spark to the microphones, or a difference in the arrival times, yields information, from which the position of the spark relative to the microphones, and hence the absolute position of the spark, is deduced, such as by triangulation. Optionally or in addition, a signal that indicates a time when the spark is produced is correlated with one or more spectra detected by a spectrometer, so a spectrum that results from the vaporized sample can be distinguished from a spectrum that results from heated gas above the sample.

25 Claims, 4 Drawing Sheets

OTHER PUBLICATIONS

Chaleaard, C., et al., "Correction of Matrix Effects in Quantitative Elemental Analysis with Laser Ablation Optical Emission Spectrometry," *Journal of Analytical Atomic Spectrometry*, vol. 12, No. 2, Feb. 1997, pp. 183-185.

International Search Report, dated Nov. 17, 2006, Received Nov. 27, 2006, PCT/US2006/027374.

GTCO GP9 Sonic Digitizer product description—PBSolutions; http://www.pbsolutions.com/gtco_gp9.html pp. 1-3, undated.

Transducer Types http://www.ndt-ed.org/EducationResources/CommunityCollege/Ultrasonics/EquipmentTra...html pp. 2-3, undated.

* cited by examiner

ARC/SPARK OPTICAL EMISSION SPECTROSCOPY CORRELATED WITH SPARK LOCATION

The present application claims priority from U.S. Provisional Patent Application, Ser. No. 60/700,664, filed c. Jul. 20, 2005, which is incorporated herein by reference.

TECHNICAL FIELD

The present invention relates to optical emission spectroscopy (OES) and, more particularly, to methods and devices for using acoustic measurements concomitant with surface ablation to obtain spatially resolved elemental analysis based on arc/spark optical emission spectroscopic techniques.

BACKGROUND ART

Optical emission spectroscopy (OES) is a mature, robust technology for the elemental analysis of materials. For metals, the prevalent techniques for generating an emission spectra use either an electric arc or a spark, or both, (collectively hereinafter "spark") to vaporize a small quantity of a sample to be analyzed. A survey of OES analytical techniques may be found in Slickers, Automatic Atomic-Emission Spectroscopy, Second Edition (1993), which is incorporated herein by reference.

Figure 1:
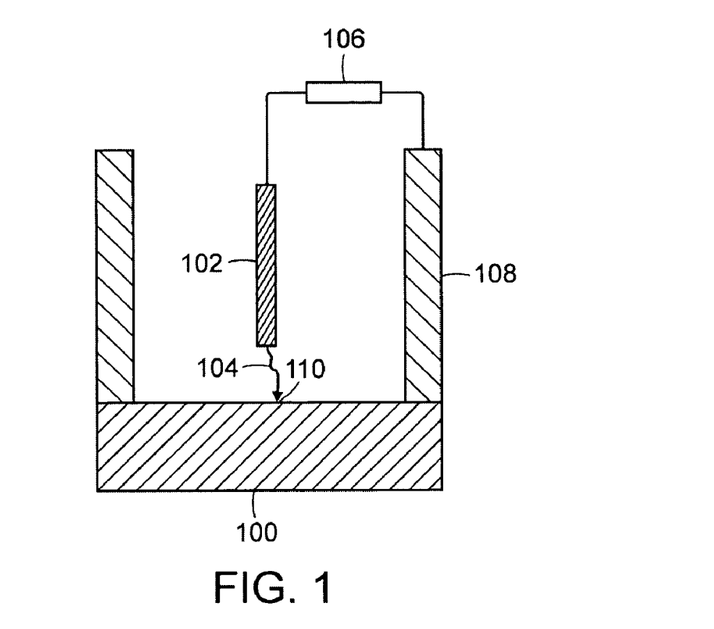
FIG. 1 is a sectioned side view block diagram of an optical emission spectroscopy (OES) arc/spark apparatus, according to the prior art.
Figure 2:
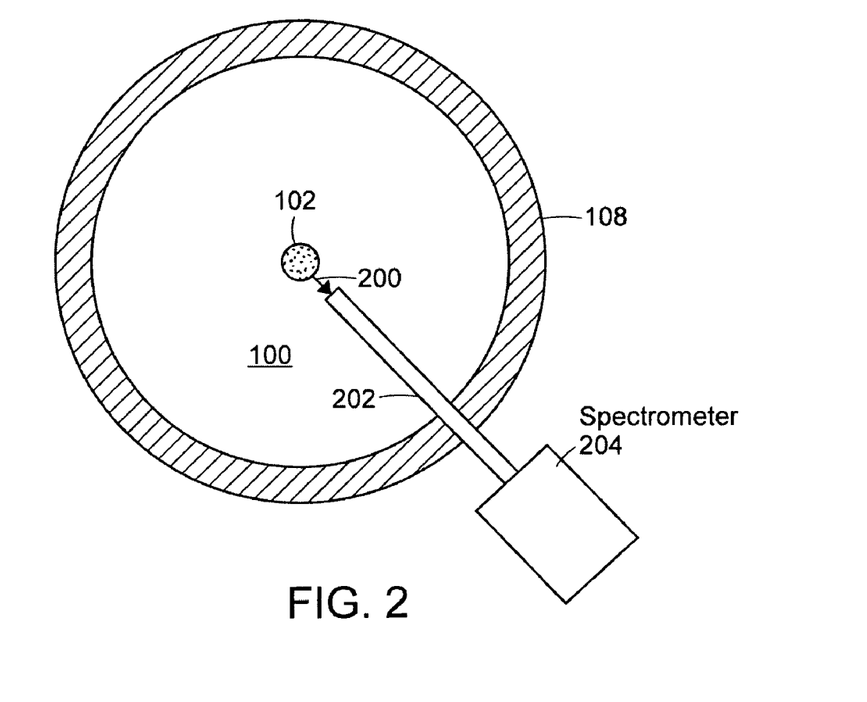
FIG. 2 is a top view block diagram of the OES arc/spark apparatus of FIG. 1.

The basic elements of the OES method are described with respect to FIGS. 1 and 2. An electrically conducting sample 100 is placed beneath an electrode 102. An arc spark 104, initiated by an appropriate electronic circuit 106, with a return path 108, vaporizes a small quantity of metal at a highly localized point 110 where the spark 104 strikes the sample 100. Monochromatic visible and/or invisible (i.e., infrared and/or ultraviolet) photo emissions 200 (FIG. 2) characteristic of elements in the vaporized metal are captured by a light guide 202, which sends the light to a spectrometer 204, which analyzes the spectrum so as to yield the elemental composition.

In order to be confident that the composition deduced from a measurement, which typically tests a miniscule portion of the sample 100, is representative of the composition of the entire sample 100, minimizing effects from, for example, inclusions, matrixes and surface contaminants, it is standard practice to average the spectra from as many as several thousand sparks that have struck an area as large as 100 square mm in the few seconds of the measurement. This large number of spark strikes typically leaves a blackened area of strike points.

Advanced techniques record and analyze the individual spectra from the thousands of sparks of a single measurement so as to eliminate outlying spectra and obtain the most confident compositional analysis of the bulk of the sample 100. At this time, however, no method exists for determining where an individual spark strikes the sample 100 and, hence, the position of an individual spark cannot be correlated with the elemental composition of the material excited by the spark.

SUMMARY OF THE INVENTION

An embodiment of the present invention provides apparatus for both analyzing composition of a sample and ascertaining a location on the sample that is analyzed using a single excitation beam. The apparatus includes a beam generator for striking at least a portion of the sample with an excitation beam. Striking the at least a portion of the sample with the beam excites the at least a portion of the sample and generates a sound. An optical signal is produced when the at least a portion of the sample is excited. The apparatus also includes a spectrometer positioned to receive the optical signal. The spectrometer generates a spectrum from the received optical signal. The apparatus also includes at least two microphones. The microphones are disposed at spaced-apart locations proximate the beam generator. The apparatus further includes a timing module coupled to the at least two microphones. The timing module is operative to ascertain a location of a source of the sound, based at least in part on timing of sound received by the at least two microphones and on the locations of the at least two microphones.

Optionally, the apparatus also includes a source of a start signal. The start signal indicates a time when the excitation beam is produced. The timing module is coupled to the source of the start signal. The timing module ascertains the location of the source of the sound, based at least in part on the start signal.

In one embodiment, the source of the start signal includes a photodiode.

In another embodiment, the source of the start signal includes at least a portion of a circuit that produces the excitation beam.

Optionally, the apparatus includes a circuit coupled to the timing module. The circuit correlates the generated spectrum with the ascertained location of the source of the sound.

In yet another embodiment, the at least two microphones include at least three microphones. The microphones are disposed at spaced-apart locations proximate the beam generator. The timing module is coupled to the at least three microphones. The timing module ascertains the location of the source of the sound, based at least in part on timing of sound received by the at least three microphones and on the locations of the at least three microphones.

In one embodiment, each of the at least two microphones includes a linear array of pressure-wave detectors.

In another embodiment, each of the at least two microphones is separated from the sample by a gaseous medium.

Alternatively, each of the at least two microphones is in mechanical contact with the sample.

In one embodiment, each of the at least two microphones is oriented perpendicular to the sample.

Alternatively, each of the at least two microphones is oriented other than perpendicular to the sample.

In one embodiment, the beam generator includes an electrode, and the excitation beam is a spark.

In another embodiment, the beam generator includes a laser.

Another embodiment of the present invention provides a method for ascertaining a location on a sample. The method includes providing a sample. At least a portion of the sample is to be analyzed for composition. The method also includes producing an excitation beam that strikes the sample. Striking the sample with the beam produces a sound and excites the at least a portion of the sample. The method also includes determining a location of a source of the sound. The location determination is based at least in part on transit times taken by the sound to reach at least two known positions. The location determination is also based at least in part on the locations of the at least two known positions.

Optionally, the method includes generating a spectrum from an optical signal produced by the excited at least a portion of the sample. In this case, the method also includes correlating the generated spectrum with the determined location of the source of the sound.

In one embodiment, producing the excitation beam includes producing a spark that strikes the sample. Producing the spark produces the sound and vaporizes the at least a portion of the sample.

In another embodiment, producing the excitation beam includes producing a laser beam that illuminates the at least a portion of the sample. Producing the laser beam and illuminating the at least a portion of the sample produces the sound and generates a plasma from the at least a portion of the sample.

Optionally, the method also includes producing an excitation beam that strikes the sample at a second known position, thereby producing a second sound. In this case, the method includes measuring a transit time taken by the second sound to reach at least one known position. Determining the location of the source of the sound is based at least in part on the measured transit time taken by the second sound to reach the at least one known position.

Yet another embodiment of the present invention provides an apparatus for correlating a spectrum generated by a spectrometer from an optical signal produced by striking a sample with an excitation beam from an beam generator. The apparatus includes a source of a start signal that indicates a time when the excitation beam is produced. The apparatus also includes a circuit that is operative to cause recording of a spectrum generated by the spectrometer at a predetermined time, relative to the start signal.

In one embodiment, the source of the start signal includes a photodiode.

In another embodiment, the source of the start signal includes at least a portion of a circuit that produces the excitation beam.

Optionally, the circuit is operative to cause the recording of the spectrum for a predetermined amount of time.

A further embodiment of the present invention provides a method for correlating a spectrum generated by a spectrometer from an optical signal produced by striking a sample with an excitation beam from an beam generator. The method includes detecting production of the excitation beam. The method also includes, in response to detecting the production of the excitation beam, identifying a spectrum generated by the spectrometer at a predetermined time, relative to detecting the production of the excitation beam.

In one embodiment, detecting production of the excitation beam includes detecting a spark.

In another embodiment, detecting production of the excitation beam includes detecting a laser beam.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS OF THE INVENTION

Embodiments of the present invention include methods and systems for determining where an individual spark strikes a sample in an OES arc/spark apparatus. Other embodiments of the present invention include methods and systems for correlating the position of an individual spark with the elemental composition of the material excited by the spark. The methods and systems described herein can determine the spatial distribution of elemental composition with great spatial resolution, such as within microns. Devices, according to the present disclosure, for making spatially correlated elemental analysis can be added to present instrumentation.

Other embodiments of the present invention include methods and systems for determining a time at which a spectrum of interest is produced or which of a plurality of spectra is of interest.

Yet other embodiments of the present invention include methods and systems for correlating the position of an individual spark with the elemental composition of the material excited by the spark.

Measuring the spatial variation of the elemental composition within a sample, as made possible by embodiments of the present invention, produces useful information, not previously available, in a single measurement. For example, such a measurement can provide information about the size and position of inclusions in an otherwise homogeneous sample. The measurement can also provide information about elemental variations across a boundary between different alloys. Such measurements and information can greatly facilitate analyzing contamination in the production or handling of metals, as well as enabling certification of spatial homogeneity of the elemental composition of a sample.

Definitions

"Excitation beam" means a stream of massive or massless particles of sufficient energy per particle to result in the detachment of an atom from the surface of a sample. Examples include, without limitation, electrons or ions in sparks, photons in laser beams, etc.

"Excite" means making a change in at least a portion of a sample as a result of striking the sample with an excitation beam, including vaporizing a portion of the sample or generating a plasma from a portion of the sample. Exciting the sample makes a change in the sample that enables analyzing composition of the sample.

"Beam generator" means an electrode, laser or other source of an excitation beam that can excite a portion of a sample sufficiently to enable atomic or molecular emissions from the excited portion to be analyzed.

Spatial Distribution of Sparks

An individual spark between an electrode and a sample generates a pressure wave in the air (or other medium) through which the spark travels and in the metal sample. In a gaseous medium, the speed of the pressure pulse equals the speed of sound in the gaseous medium; in pure air at standard temperature and pressure, the sound speed is about $33.180 \times 10^3$ cm/sec. The speeds in metals vary with the composition and temperature of the metals. For example, the speed in steel at 20° C. is about $4.4 \times 10^5$ cm/sec. The speeds in other metals are well known to, or can be determined by, those of ordinary skill in the art.

In embodiments of the present invention, two or more high-frequency microphones are placed appropriately in a gaseous medium, or appropriately on the metal sample, or on both the sample and in the gas. Arrival times of the sound from the spark to the microphones, or a difference in the arrival times, yields information, from which the position of the spark relative to the microphones, and hence the absolute position of the spark, can be deduced, such as by triangulation. The precise speed of the sound in the gas and in the metal can be determined during the measurement by generating a fiducial "cold" spark at a fixed and accurately known position with respect to the microphones. Thus, the apparatus can be calibrated using the fiducial spark.

Measuring Transit Times in a Gaseous Medium

Figure 3:
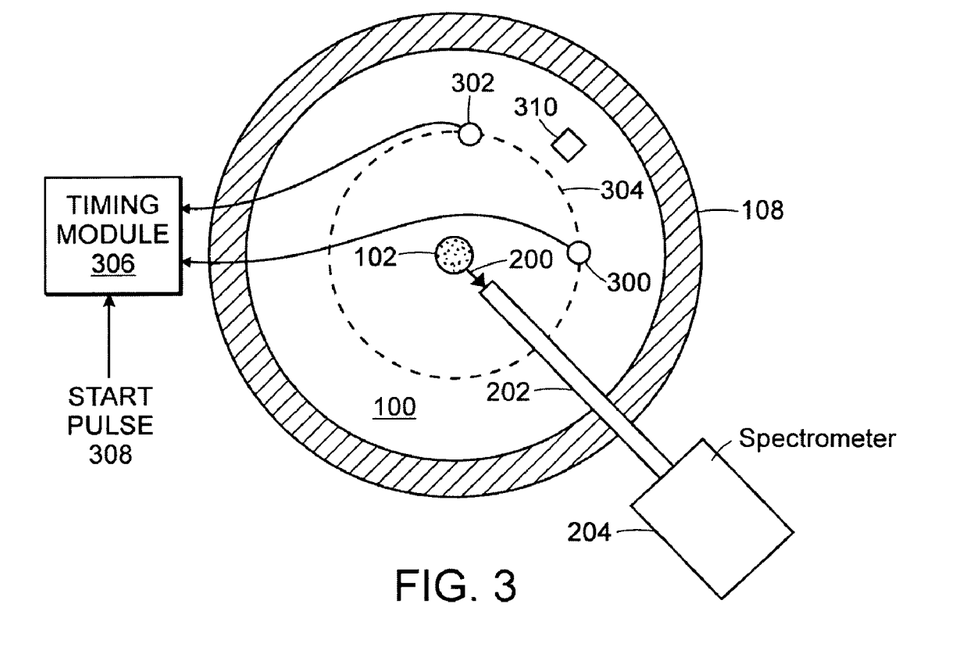
FIG. 3 is a top view block diagram of a system for determining where a spark strikes a sample in an OES arc/spark apparatus, according to one embodiment of the present invention.
Figure 4:
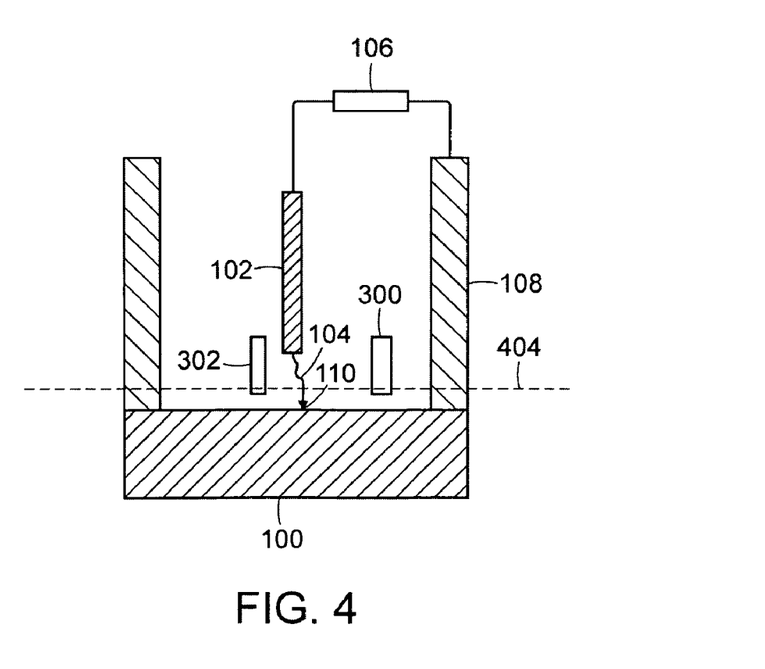
FIG. 4 is a sectioned side view block diagram of the system of FIG. 3.

One embodiment of the present invention is shown in a top view block diagram in FIG. 3 and in a sectioned side view block diagram in FIG. 4. For simplicity, FIGS. 3 and 4 show only two microphones 300 and 302; however, other numbers of microphones can be used. In general, more microphones provide more accuracy than fewer microphones. The two microphones 300 and 302, preferably with bandwidths in the megahertz or greater range, are placed in a plane 404 (FIG. 4) that is parallel to the sample 100 and that intersects a spark gap between the electrode 102 and the sample 100. The microphones 300 and 302 are not in mechanical contact with the sample 100; that is, the microphones 300 and 302 are separated from the sample 100 by a gaseous medium, such as air at standard temperature and pressure.

In some embodiments, the microphones 300 and 302 are about 90° apart on a circle 304 (FIG. 3) that has a radius of, for example, about 3 cm from the center line of the electrode 102 and centered on the electrode 102. In other embodiments, the microphones 300 and 302 are placed at other angles and/or along circles having other radii. For example, three microphones (not shown) can be placed about 120° apart on a circle.

Microphone signals are sent to a timing module 306 that measures transit times of the sound waves from the spark 104 to the microphones 300 and 302. A pulse (start pulse 308) that signals the start of the spark 104 can be obtained from the electronics 106 that initiates the spark 104, from a light signal from the spark 104 picked up by a photodiode or another suitable device 310 placed anywhere near the discharge or from another appropriate source. The velocity of the sound wave in the air, as measured by a fiduciary spark or noise generator, is taken to be 33,180 cm/sec.

Consider the timing of the sound from a spark that strikes the sample 100 precisely below the center line of the electrode 102. A sound travels through the air to the microphones 300 and 302. A sound signal from each of the microphones 300 and 302 enters the timing module 306 about 90.42 µsec. after the start pulse 308:

$$3 \text{ cm}/33,180 \text{ cm/sec.} = 90.42 \text{ µsec.}$$

With a timing uncertainty of about 0.1 µsec., the X and Y positions of the spark, as determined by the signals from the microphones 300 and 302, can be calculated to an accuracy of about:

$$(10^{-7}/90.42) \times 10^{-6} \times 3 = 3.32 \times 10^{-3} \text{ cm}$$

Commercial timing circuits used for pulsed ultrasound (such as those used in non-destructive testing) have uncertainties of less than about 1 nanoseconds. Thus, with an appropriate timing circuit, the location (such as X and Y coordinates) of the spark can be determined to within at least about 4 microns. The determined location of the spark 104 can be correlated with the spectrum generated by the spectrometer 204. Thus, the compositional analysis can be correlated with the location on the sample 100 that was analyzed.

The spark 104 is, however, unlikely to travel in a straight line perpendicular to the sample 100. A pressure wave is generated along the entire spark 104. This pressure wave arrives, therefore, over a range of times at each microphone 300 and 302, leading to an uncertainty in the measurement of the spark position. The angle of the spark 104, and hence the position that the spark strikes the sample 100, may be determined by analyzing the waveforms from two or more microphones using well-known signal processing techniques. For example, three microphones (not shown) can be positioned 120° apart along the circle 304.

Alternatively, each microphone can be replaced with a linear array of pressure-wave detectors oriented perpendicular to the surface of the sample 100, the length of the array being approximately equal to the width of the spark gap, i.e., the distance between the electrode 104 and the sample 100.

Although air at standard temperature and pressure is used in this embodiment, in other embodiments, other gaseous media, temperatures and/or pressures can be used. Of course, the calculations described above are altered to take into account the speed of sound in the selected gas at the selected temperature and pressure.

Although in the above-described embodiment the microphones 300 and 302 are placed on a circle centered on the electrode 102, in other embodiments the microphones 300 and 302 are not placed on a circle. That is, the distances between the center line of the electrode 102 and the microphones 300 and 302 are not equal. In such embodiments, calculations of the spark locations are altered to take into account the differences in sound path lengths to the microphones 300 and 302.

Measuring Transit Times in the Sample

Figure 5:
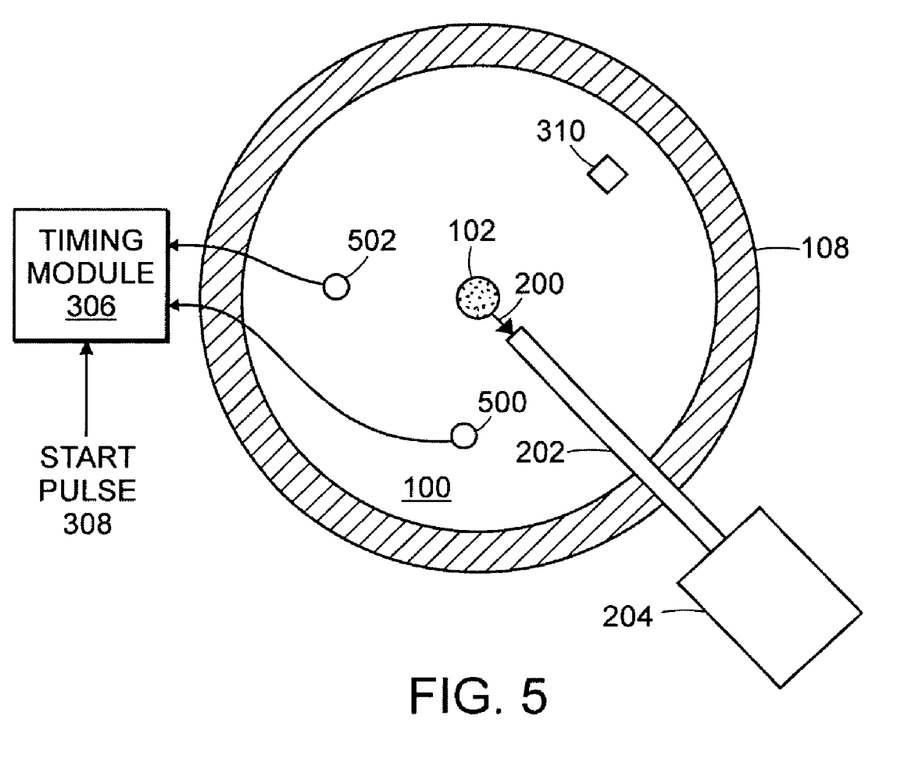
FIG. 5 is a top view block diagram of a system for determining where a spark strikes a sample in an OES arc/spark apparatus, according to another embodiment of the present invention.
Figure 6:
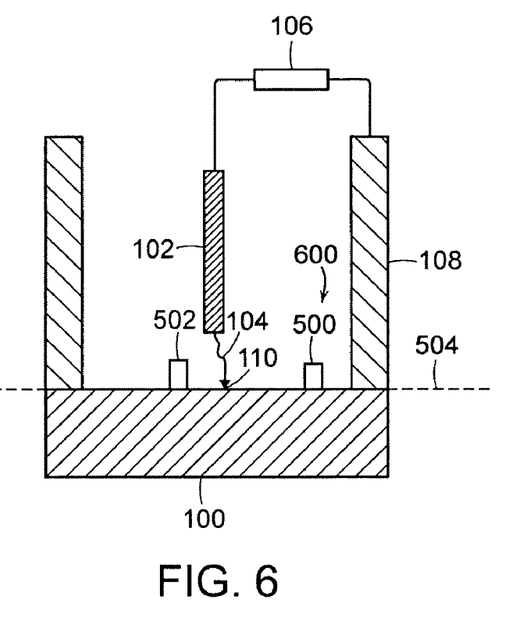
FIG. 6 is a sectioned side view block diagram of the system of FIG. 5.

Another embodiment of the present invention is shown in a top view block diagram in FIG. 5 and in a sectioned side view block diagram in FIG. 6. For simplicity, FIGS. 5 and 6 show only two microphones 500 and 502 or other types of pressure sensors or transducers (collectively referred to herein as microphones); however, other numbers of microphones can be used. In this embodiment, the microphones 500 and 502 are mechanically attached to the sample 100, and sound travel times within the sample 100 are measured. Measuring sound transit times in the sample 100 can provide more accurate X and Y positions of the sparks 104 than by measuring sound transit times in a gaseous medium. Embodiments that measure sound transit times within the sample 100 are currently preferred.

The microphones 500 and 502 are pressed to the sample 100 on the plane 504 in which the spark 104 strikes the sample 100. The microphones 500 and 502 are in mechanical contact with the sample 100, either directly or through an intermediate substance, such as a wear plate, wedge (described below), sound-conductive grease or the like. The microphones are preferably about 90° apart on a circle whose center is on the centerline of the electrode 102. However, as discussed above, other angles, radii and unequal microphone-to-electrode spacings can be used.

The sound wave in the sample 100 is initiated at a point where the spark 104 strikes the sample 100, and the sound wave travels from that point to the microphones 500 and 502. As discussed above, the start pulse 308 signals the start of the spark 104. The timing module 306 measures transit times of the sound waves from the spark 104 strike location to the microphones 300 and 302, or differences in the transit times. The X and Y positions of the point where the spark 104 strikes the sample 100 are calculated based on the transit times, or a difference in transit times, of the sounds at the microphones 500 and 502. The speed of the sound wave in the sample 100 can be measured using a fiduciary spark or noise generator, and this measured speed can be used in the position determination.

The microphones 500 and 502 may detect sound (from the spark 104) that travels through the gaseous medium above the sample 100, in addition to the sound that travels within the sample 100. Thus, the microphones 500 and 502 may detect superfluous sounds. The speed of sound traveling in the sample 100 is typically more than an order of magnitude higher than the speed of sound traveling in the gaseous medium above the sample 100. Thus, the sound that travels through the gaseous medium arrives at the microphones 500 and 502 considerably later than the sound that travels through the sample 100.

Optionally, a circuit (not shown) discriminates between sounds that travel through the gaseous medium and sounds that travel through the sample 100, and the circuit ignores sounds that travel through the gaseous medium. For example, the circuit can ignore sounds that travel for more than a predetermined amount of time (i.e., arrive at the microphone 500 or 502 more than a predetermined amount of time after the start pulse 308 signal), where the predetermined amount of time is approximately equal to the amount of time required for a sound wave to travel from the point 110 where the spark 104 strikes the sample 100 to the furthest edge of the sample 100. Alternatively, the circuit can react to the first sound detected by each microphone 500 and 502 and ignore subsequent sounds detected by each of the microphones until after the circuit receives a subsequent start pulse 308 signal.

Figure 7:
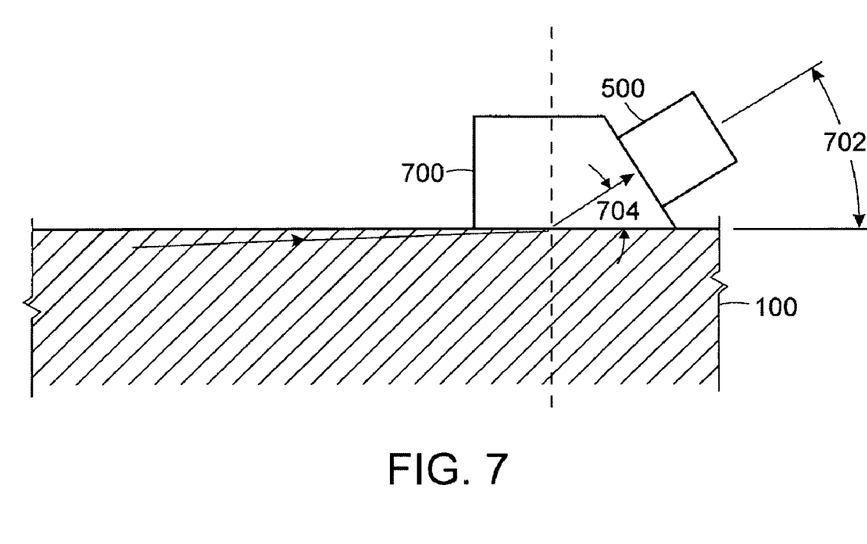
FIG. 7 is an enlarged view of a portion of FIG. 6.

The microphones 500 and 502 can be oriented perpendicular to the surface of the sample 100. Alternatively, as shown in FIG. 7, a wedge 700 can be used to orient each microphone 500 and 502 at an angle 702 to the surface of the sample 100. (FIG. 7 is an enlarged, sectioned view of a portion 600 of FIG. 6.) Orienting the microphones 500 and 502 at an angle 702 that corresponds to, or approximates, an angle of refraction 704 of the sound as it transits the boundary between the sample 100 and the wedge 700 directs a larger fraction of the sound to the microphone 500.

Microphones and Transducers

Ultrasonic techniques for non-destructive testing (NDT) of metals is a mature technology with a vast literature. For example, a tutorial of basic principles, methods and applications related to NDT is available at www.ndt-ed.org, the contents of which are hereby incorporated by reference.

Transducers with time resolutions of about $10^{-10}$ secs. are used in the NDT arts. Using such transducers, sub-micron accuracy in determining the spark position, and hence the atomic composition of the vaporized material at that point, is possible. Using such transducers, it is possible to measure the time between the start pulse 308 and the sound of the spark 104 reaching the microphone 500 or 502 to within about a nanosecond, and quite possibly less. For example, if the mean distance from the spark 104 to the microphone 500 or 502 is about 2 cm, the transit time is about 4 microseconds, and the uncertainty in the measured distance could be as small as about 5 microns for a 1 nanosecond timing resolution:

$$2\,\text{cm} \times (10^{-9}\,\text{sec.})/(4 \times 10^{-6}\,\text{sec.}) = 5 \times 10^{-4}\,\text{cm}$$

Correlating Spark Time with Spectrum

Various spectra are produced as a result of the spark 104 striking the sample 100. The spectra can include visible and invisible, such as infrared and/or ultraviolet, light. The spectrum of interest is produced when a portion of the sample 100 is vaporized by the spark 104. However, before and/or after the portion of the sample 100 is vaporized, heated or ionized gas above the point 110 where the spark 104 strikes the sample 100 also produces a spectrum, which is of little or no interest and can lead to an incorrect analysis of the composition of the sample 100.

In some embodiments of the present invention, the time of the spark 104 is correlated with various spectra detected by the spectrometer 204, so the spectrum that results from the vaporized sample 100 can be distinguished from the spectrum/a that results from the heated gas. Correlating the time of the spark 104 and the spectrum can reduce or eliminate the need to flush the spark gap, such as with argon, prior to producing the spark 104, as was commonly done to prevent or reduce the unwanted spectrum produced by the heated gas above the sample 100.

In one such embodiment, the start pulse 308, or another time signal produced as a result of, or in concert with, the spark 104, triggers the spectrometer 204 to record the spectrum detected by the spectrometer 204 at the time of the signal. Optionally, the time signal to the spectrometer can be delayed by a suitable amount of time, such that the spectrum detected by the spectrometer at the time of the signal is the spectrum of interest. For example, the spectrum of interest may be one that is detected at a predetermined amount of time after the spark 104 strikes the sample 100. This delay can be dependant on the angle of the spark 104, and hence the position that the spark strikes the sample 100, as determined by analyzing the waveforms from the microphones.

Once triggered, the spectrometer 204 can record a single spectrum, or the spectrometer 204 can record spectra for a predetermined amount of time.

In another such embodiment, the spectrometer 204 records (such as in a general- or special-purpose computer, not shown) the spectra, along with timestamps indicating when each spectrum is generated. The time of the spark 104 and, optionally, the time at which the spark 104 strikes the sample 100, is/are also recorded. Then, the recorded spectra and the time of the spark (or strike) are correlated to select the spectrum/a of interest.

Laser-Induced Optical Emissions

Instead of a spark, another excitation phenomena can be used to excite a sample and produce a spectrum that can be analyzed. For example, one or more lasers can be used to excite a sample or a portion thereof. The portion of the sample illuminated by the laser can be vaporized or a plasma can be generated from the portion of the sample. The methods and systems described herein can be used to determine the location where the laser or other energy beam strikes the sample.

The term "excitation beam" is used herein to refer to sparks, laser beams and other excitation phenomena that can be used to excite a sample. The term "excite" is used herein to refer to the effect of striking a sample with an excitation beam, including vaporizing a portion of the sample or generating a plasma from a portion of the sample such as to facilitate analyzing the composition of the portion of the sample that is excited. The term "beam generator" is used to refer to an electrode, laser or other source of an excitation beam.

CONCLUSION

As noted, sometimes many (sometimes thousands of) spectra are collected from a single sample. Because each spark strike tends to leave a layer of electrically insulating material, subsequent sparks are not likely to strike previously struck locations on the sample. Thus, the sparks tend to be distributed over an area of the sample.

Using the methods and apparatus described herein, the location of each spark strike can be correlated with its corresponding spectrum. Hence, the elemental composition of the material excited by each spark can be correlated with the location of the spark strike. Consequently, the spatial distribution of elemental composition within the sample can be determined. The spatial distribution of elemental composition can provide information about the size and position of inclusions in an otherwise homogeneous sample. This data can also provide information about elemental variations across a boundary between different alloys. Such measurements and information can greatly facilitate analyzing contamination in the production or handling of metals, as well as enabling certification of spatial homogeneity of the elemental composition of a sample.

Both the location of an excitation beam strike and the elemental composition of the sample at the strike site can be determined by a single beam strike. This provides an economical and accurate system.

While the invention is described through the above-described exemplary embodiments, it will be understood by those of ordinary skill in the art that modifications to, and variations of, the illustrated embodiments may be made without departing from the inventive concepts disclosed herein. Moreover, while the preferred embodiments are described in connection with various microphones, transducers and pressure sensors, one skilled in the art will recognize that the system and methods may be embodied using a variety of sensors capable of detecting sound or a pressure wave. Accordingly, the invention should not be viewed as limited, except by the scope and spirit of the appended claims.

I/we claim:

1. An apparatus for both analyzing composition of a sample and ascertaining a location on the sample that is analyzed using a single excitation beam, comprising:
   a beam generator for striking at least a portion of the sample with an excitation beam, thereby exciting the at least a portion of the sample and generating a sound;
   a spectrometer positioned to receive an optical signal produced when the at least a portion of the sample is excited and generate a spectrum from the received optical signal;
   at least two microphones disposed at spaced-apart locations proximate the beam generator; and
   a timing module coupled to the at least two microphones and operative to ascertain a location of a source of the sound, based at least in part on timing of sound received by the at least two microphones and on the locations of the at least two microphones.

2. The apparatus defined by claim 1, further comprising a source of a start signal that indicates a time when the excitation beam is produced; and wherein the timing module is coupled to the source of the start signal and operative to ascertain the location of the source of the sound, based at least in part on the start signal.

3. The apparatus defined by claim 2, wherein the source of the start signal comprises a photodiode.

4. The apparatus defined by claim 2, wherein the source of the start signal comprises at least a portion of a circuit that produces the excitation beam.

5. The apparatus defined by claim 1, further comprising a circuit coupled to the timing module and operative to correlate the generated spectrum with the ascertained location of the source of the sound.

6. The apparatus defined by claim 1, wherein:
   the at least two microphones comprise at least three microphones disposed at spaced-apart locations proximate the beam generator; and
   wherein the timing module is coupled to the at least three microphones and is operative to ascertain the location of the source of the sound, based at least in part on timing of sound received by the at least three microphones and on the locations of the at least three microphones.

7. The apparatus defined by claim 1, wherein each of the at least two microphones comprises a linear array of pressure-wave detectors.

8. The apparatus defined by claim 1, wherein each of the at least two microphones is separated from the sample by a gaseous medium.

9. The apparatus defined by claim 1, wherein each of the at least two microphones is in mechanical contact with the sample.

10. The apparatus defined by claim 9, wherein each of the at least two microphones is oriented perpendicular to the sample.

11. The apparatus defined by claim 9, wherein each of the at least two microphones is oriented other than perpendicular to the sample.

12. The apparatus defined by claim 1, wherein the beam generator comprises an electrode and the excitation beam comprises a spark.

13. The apparatus defined by claim 1, wherein the beam generator comprises a laser.

14. The apparatus defined by claim 1, further comprising:
   a source of a start signal that indicates a time when the excitation beam is produced; and
   a circuit operative to cause recording of a spectrum generated by the spectrometer at a predetermined time, relative to the start signal.

15. The apparatus defined by claim 14, wherein the source of the start signal comprises a photodiode.

16. The apparatus defined by claim 14, wherein the source of the start signal comprises at least a portion of a circuit that produces the excitation beam.

17. The apparatus defined by claim 14, wherein the circuit is operative to cause the recording of the spectrum for a predetermined amount of time.

18. A method for ascertaining a location on a sample, comprising:
   providing a sample, at least a portion of which is to be analyzed for composition;
   producing an excitation beam that strikes the sample, thereby producing a sound and exciting the at least a portion of the sample;
   determining a location of a source of the sound, based at least in part on transit times taken by the sound to reach at least two known positions and on the locations of the at least two known positions.

19. The method defined by claim 18, further comprising:
generating a spectrum from an optical signal produced by the excited at least a portion of the sample; and
correlating the generated spectrum with the determined location of the source of the sound.

20. The method defined by claim 18, wherein producing the excitation beam comprises producing a spark that strikes the sample, thereby producing the sound and vaporizing the at least a portion of the sample.

21. The method defined by claim 18, wherein producing the excitation beam comprises producing a laser beam that illuminates the at least a portion of the sample, thereby producing the sound and generating a plasma from the at least a portion of the sample.

22. The method defined by claim 18, further comprising:
producing an excitation beam that strikes the sample at a second known position, thereby producing a second sound; and
measuring a transit time taken by the second sound to reach at least one known position; and
wherein determining the location of the source of the sound is based at least in part on the measured transit time taken by the second sound to reach the at least one known position.

23. The method defined by claim 14, further comprising:
detecting production of the excitation beam;
responsive to detecting the production of the excitation beam, identifying a spectrum generated by the spectrometer at a predetermined time, relative to detecting the production of the excitation beam.

24. The method defined by claim 23, wherein detecting production of the excitation beam comprises detection of a spark.

25. The method defined by claim 23, wherein detecting production of the excitation beam comprises detection of a laser beam.

* * * * *

UNITED STATES PATENT AND TRADEMARK OFFICE
CERTIFICATE OF CORRECTION

PATENT NO. : 7,391,508 B2
APPLICATION NO. : 11/486439
DATED : June 24, 2008
INVENTOR(S) : Lee Grodzins

Page 1 of 1

It is certified that error appears in the above-identified patent and that said Letters Patent is hereby corrected as shown below:

In Col. 12, line 7
replace "claim 14"
with --claim 18--

Signed and Sealed this

Twenty-sixth Day of August, 2008

JON W. DUDAS
*Director of the United States Patent and Trademark Office*